US012465337B2

(12) United States Patent
McBreen et al.

(10) Patent No.: US 12,465,337 B2
(45) Date of Patent: Nov. 11, 2025

(54) NEEDLE ROTATION MECHANISM FOR BIOPSY NEEDLE

(71) Applicant: Devicor Medical Products, Inc., Cincinnati, OH (US)

(72) Inventors: David C. McBreen, Cincinnati, OH (US); Justin Rebellino, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 926 days.

(21) Appl. No.: 17/324,330

(22) Filed: May 19, 2021

(65) Prior Publication Data

US 2021/0275156 A1 Sep. 9, 2021

Related U.S. Application Data

(63) Continuation of application No. PCT/US2019/062162, filed on Nov. 19, 2019.

(60) Provisional application No. 62/769,944, filed on Nov. 20, 2018.

(51) Int. Cl.
*A61B 10/02* (2006.01)

(52) U.S. Cl.
CPC .. *A61B 10/0266* (2013.01); *A61B 2010/0208* (2013.01)

(58) Field of Classification Search
CPC ........ A61B 10/0266; A61B 2010/0208; A61B 10/0283; A61B 10/0275
See application file for complete search history.

(56) References Cited

U.S. PATENT DOCUMENTS

| | | | |
|---|---|---|---|
| 5,526,822 | A | 6/1996 | Burbank et al. |
| 6,086,544 | A | 7/2000 | Hibner et al. |
| 6,602,203 | B2 | 8/2003 | Stephens et al. |
| 6,626,849 | B2 | 9/2003 | Huitema et al. |
| 7,442,171 | B2 | 10/2008 | Stephens et al. |
| 7,854,706 | B2 | 12/2010 | Hibner |
| 8,083,687 | B2 | 12/2011 | Parihar |

(Continued)

FOREIGN PATENT DOCUMENTS

| | | | |
|---|---|---|---|
| CN | 1655724 | A | 8/2005 |
| CN | 101237822 | A | 8/2008 |

(Continued)

OTHER PUBLICATIONS

Chinese Office Action dated Apr. 27, 2023 for Application No. 201980076302.8, 8 pages.

(Continued)

*Primary Examiner* — Jason M Sims
*Assistant Examiner* — Kyle W. Kretzer
(74) *Attorney, Agent, or Firm* — Frost Brown Todd LLP

(57) ABSTRACT

A biopsy device includes a probe, a needle, a cutter, and a manually actuated needle rotation assembly. The probe includes a probe housing. The needle extends from the probe. The cutter is disposed within the needle. The cutter defines a cutter lumen and at least partially defines a vent lumen between an exterior of the cutter and an interior of the needle. The needle rotation assembly includes a pinion shaft. A portion of the pinion shaft is exposed relative to the probe housing such that the pinion shaft is configured for actuation using a single hand while grasping the biopsy device with the single hand.

16 Claims, 13 Drawing Sheets

(56) References Cited

U.S. PATENT DOCUMENTS

| | | | | |
|---|---|---|---|---|
| 8,206,316 B2 | 6/2012 | Hibner et al. | | |
| 8,764,680 B2 | 7/2014 | Rhad et al. | | |
| 8,801,742 B2 | 8/2014 | Hibner et al. | | |
| 9,095,326 B2 | 8/2015 | Ritchie et al. | | |
| 9,345,457 B2 | 5/2016 | Speeg et al. | | |
| 9,999,406 B2 | 6/2018 | Hibner et al. | | |
| 10,206,665 B2 | 2/2019 | Fiebig et al. | | |
| 2006/0074345 A1 | 4/2006 | Hibner | | |
| 2010/0152610 A1 | 6/2010 | Parihar et al. | | |
| 2010/0160822 A1 | 6/2010 | Parihar et al. | | |
| 2010/0160826 A1* | 6/2010 | Parihar | A61B 10/0275 | 600/567 |
| 2012/0109007 A1* | 5/2012 | Rhad | A61B 10/0096 | 600/567 |
| 2012/0130275 A1* | 5/2012 | Chudzik | A61B 10/0283 | 600/567 |
| 2015/0148703 A1* | 5/2015 | Fiebig | A61B 10/0283 | 600/567 |

FOREIGN PATENT DOCUMENTS

| | | |
|---|---|---|
| CN | 103932743 A | 7/2014 |
| CN | 104968282 A | 10/2015 |
| CN | 105769254 A | 7/2016 |

OTHER PUBLICATIONS

Chinese Office Action dated Dec. 12, 2023 for Application No. 201980076302.8, 7 pages.

International Search Report and Written Opinion dated Jun. 23, 2020 for Application No. PCT/US2019/062162, 16 pages.

* cited by examiner

NEEDLE ROTATION MECHANISM FOR BIOPSY NEEDLE

PRIORITY

This application claims priority to U.S. Provisional Patent App. No. 62/769,944 entitled "Needle Rotation Mechanism for Biopsy Needle," filed on Nov. 20, 2018, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 30, 2003; U.S. Pat. No. 7,442,171, entitled "Remote Thumbwheel for a Surgical Biopsy Device," issued Oct. 28, 2008; U.S. Pat. No. 8,764,680, entitled "Handheld Biopsy Device with Needle Firing," issued Jul. 7, 2014; U.S. Pat. No. 9,345,457, entitled "Presentation of Biopsy Sample by Biopsy Device, issued May 24, 2016; U.S. Pub. No. 2006/0074345, entitled "Biopsy Apparatus and Method," published Apr. 6, 2006, now abandoned; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; and U.S. Pub. No. 2012/0310110, entitled "Needle Assembly and Blade Assembly for Biopsy Device," published Dec. 6, 2012. The disclosure of each of the above-cited U.S. Pat. Nos., U.S. Patent Application Publications, and U.S. Non-Provisional Patent Applications is incorporated by reference herein.

In some circumstances, it may be desirable to rotate a biopsy needle while collecting tissue samples. For instance, in some circumstances a lateral aperture used to collect tissue samples is positioned within or adjacent to a suspect lesion. In such examples, it may be desirable to collect a tissue sample from each region 360° around the needle in order to collect the entire lesion as well as the margins between the lesion and healthy tissue.

In contexts where needle rotation is desired, it may also be desirable to rotate the needle using a single hand. For instance, in some contexts one hand is used to hold the biopsy device while another hand is used to hold another instrument such as an ultrasound transducer. Thus, with both hands occupied, it may be desirable to rotate the needle with the hand holding the biopsy device to avoid having to release either the biopsy device itself or other instruments used in the biopsy procedure.

While several systems and methods have been made and used for obtaining a biopsy sample, it is believed that no one prior to the inventors has made or used the invention described in the appended claims.

BRIEF DESCRIPTION OF THE FIGURES

While the specification concludes with claims which particularly point out and distinctly claim the biopsy device, it is believed the present biopsy device will be better understood from the following description of certain examples taken in conjunction with the accompanying drawings, in which like reference numerals identify the same elements and in which:

DETAILED DESCRIPTION

The following description of certain examples of the biopsy device should not be used to limit the scope of the present biopsy device. Other examples, features, aspects, embodiments, and advantages of the biopsy device will become apparent to those skilled in the art from the following description, which is by way of illustration, one of the best modes contemplated for carrying out the biopsy device. As will be realized, the biopsy device is capable of other different and obvious aspects, all without departing from the spirit of the biopsy device. Accordingly, the drawings and descriptions should be regarded as illustrative in nature and not restrictive.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

I. Overview of Exemplary Biopsy Device

Figure 1:
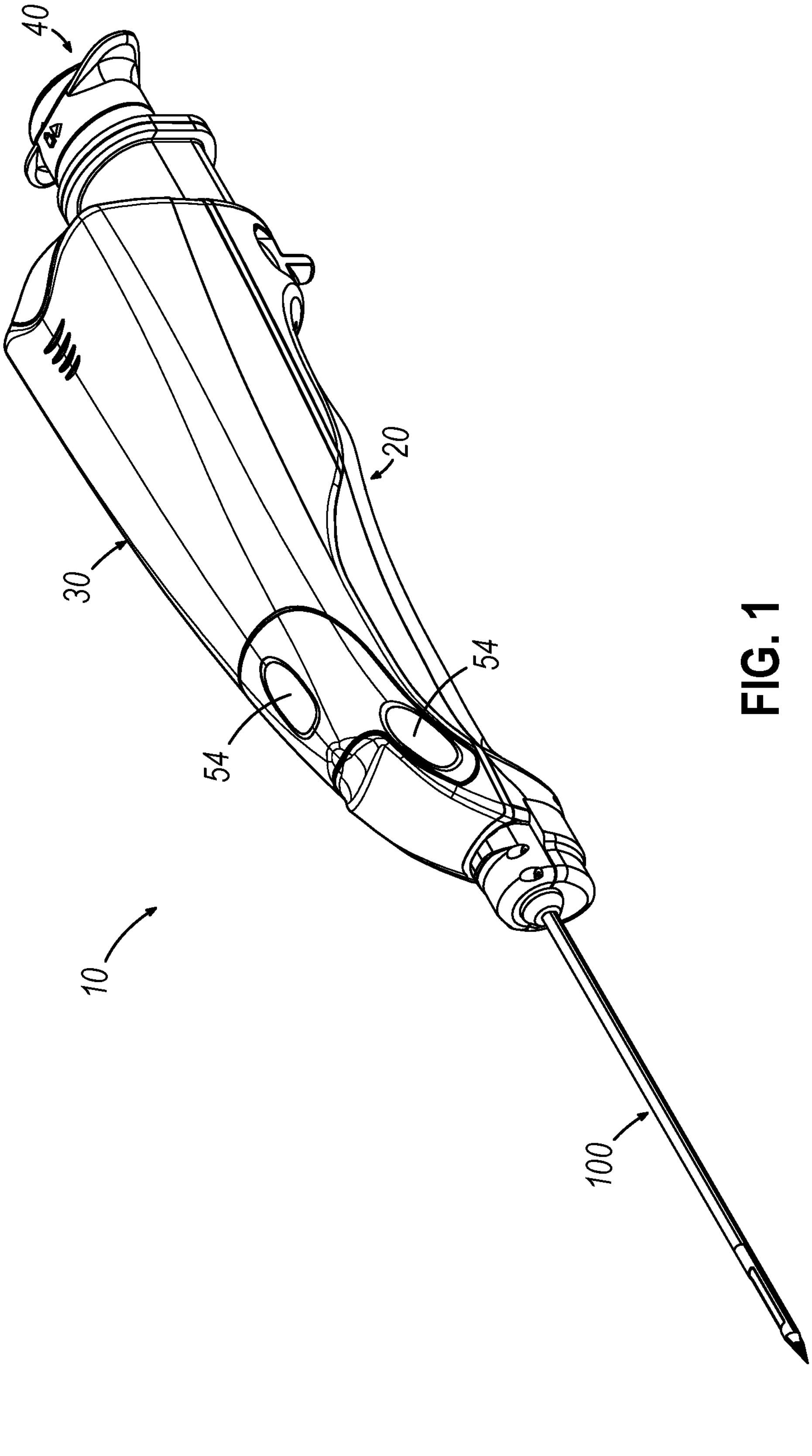
FIG. 1 depicts a perspective view of an exemplary biopsy device.
Figure 2:
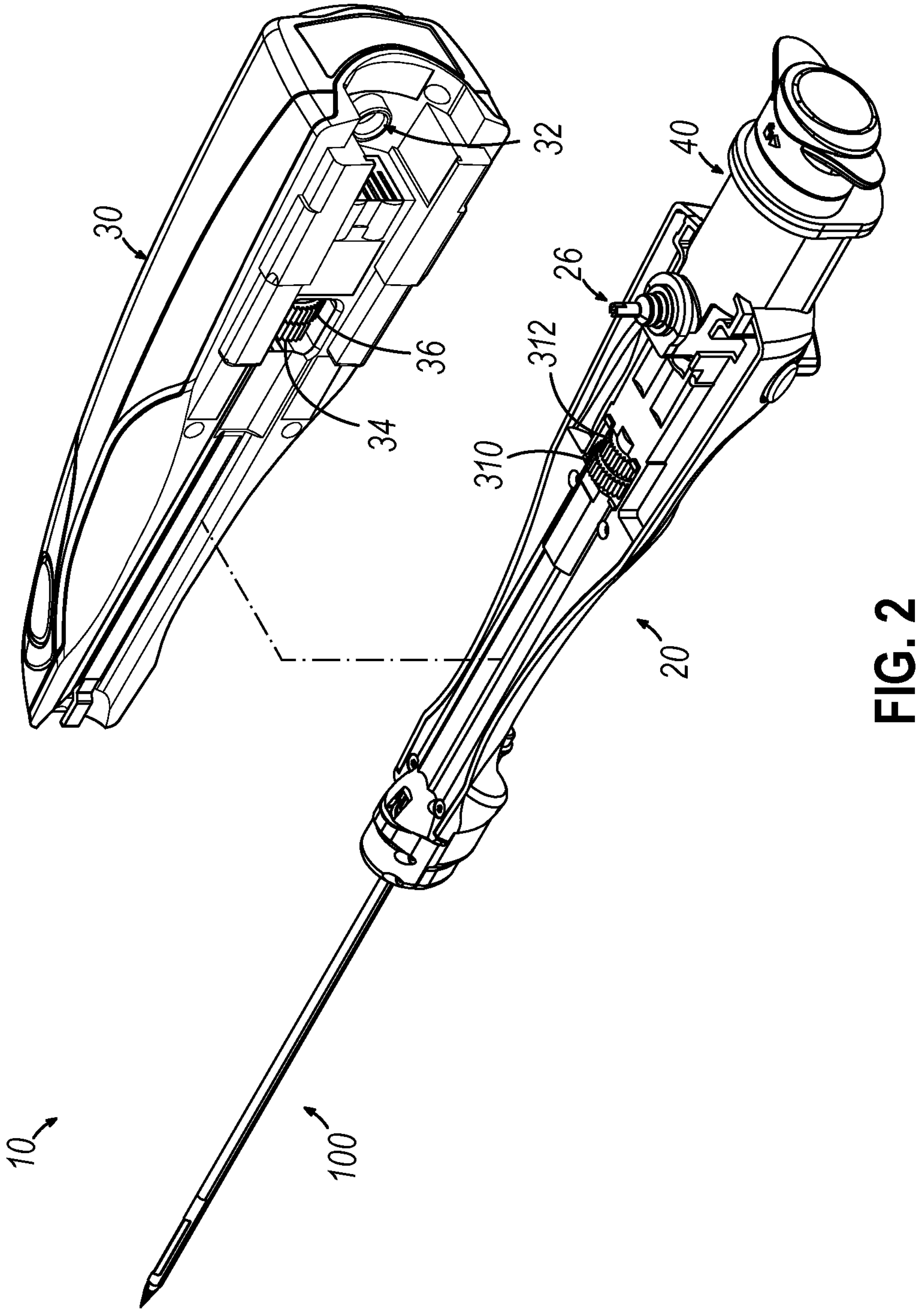
FIG. 2 depicts a perspective view of the biopsy device of FIG. 1, showing a holster detached from a probe.

FIG. 1 shows an exemplary biopsy device (10), comprising a probe (20) and a holster (30). Probe (20) comprises a needle assembly (100) that at least partially extends distally from a casing of probe (20). Needle assembly (100) is insertable into a patient's tissue to obtain tissue samples as will be described below. Biopsy device (10) further comprises a tissue sample holder (40) into which the tissue samples are deposited. By way of example only, probe (20) may be a disposable component and holster (30) may be a reusable component to which probe (20) may be coupled, as is shown in FIG. 2. Use of the term "holster" herein should not be read as requiring any portion of probe (20) to be inserted into any portion of holster (30). Indeed, in one configuration for biopsy device (10), probe (20) may simply be positioned atop holster (30). Alternatively, a portion of probe (20) may be inserted into holster (30) to secure probe (20) to holster (30). In yet another configuration, a portion of holster (30) may be inserted into probe (20). Further still, probe (20) and holster (30) may be integrally formed as a single unit.

In configurations where probe (20) and holster (30) are separable members, a port and/or a seal (32) may be provided on holster (30) to couple with a second port and/or a seal (26) on probe (20) such that the vacuum produced by a vacuum pump (50) within holster (30) may be fluidly connected to probe (20). Holster (30) may also provide gears (34, 36) which mate to and engage with gears (310, 312) on probe (20). It should be understood that the configuration depicted in FIG. 2 that communicates vacuum and motive force between holster (30) and probe (20) is merely exemplary. In some versions, such configurations may be constructed in accordance with at least some of the teachings of U.S. Pat. No. 8,206,316 entitled "Tetherless Biopsy Device with Reusable Portion," issued Jun. 26, 2012; and/or U.S. Pub. No. 2012/0065542, entitled "Biopsy Device Tissue Sample Holder with Removable Tray," published Mar. 15, 2012, the disclosures of which are incorporated by reference herein.

With holster (30) and probe (20) connected, vacuum pump (50) can induce a vacuum within needle assembly (100) via tissue sample holder (40) and a tubular cutter (60). However, it should be understood that vacuum may be provided in other ways. For example, vacuum pump (50) may be independent of holster (30) and probe (20) and may simply be coupled by vacuum tubes to appropriate ports on biopsy device (10). Biopsy device (10) may further be configured in accordance with at least some of the teachings of U.S. Pat. No. 8,764,680, entitled "Handheld Biopsy Device with Needle Firing," issued Jul. 1, 2014; and/or U.S. Pub. No. 2012/0065542, entitled "Biopsy Device Tissue Sample Holder with Removable Tray," published Mar. 15, 2012, the disclosures of which are incorporated by reference herein. Other suitable structural and functional combinations for probe (20) and holster (30) will be apparent to one of ordinary skill in the art in view of the teachings herein.

II. Exemplary Holster

Figure 3:
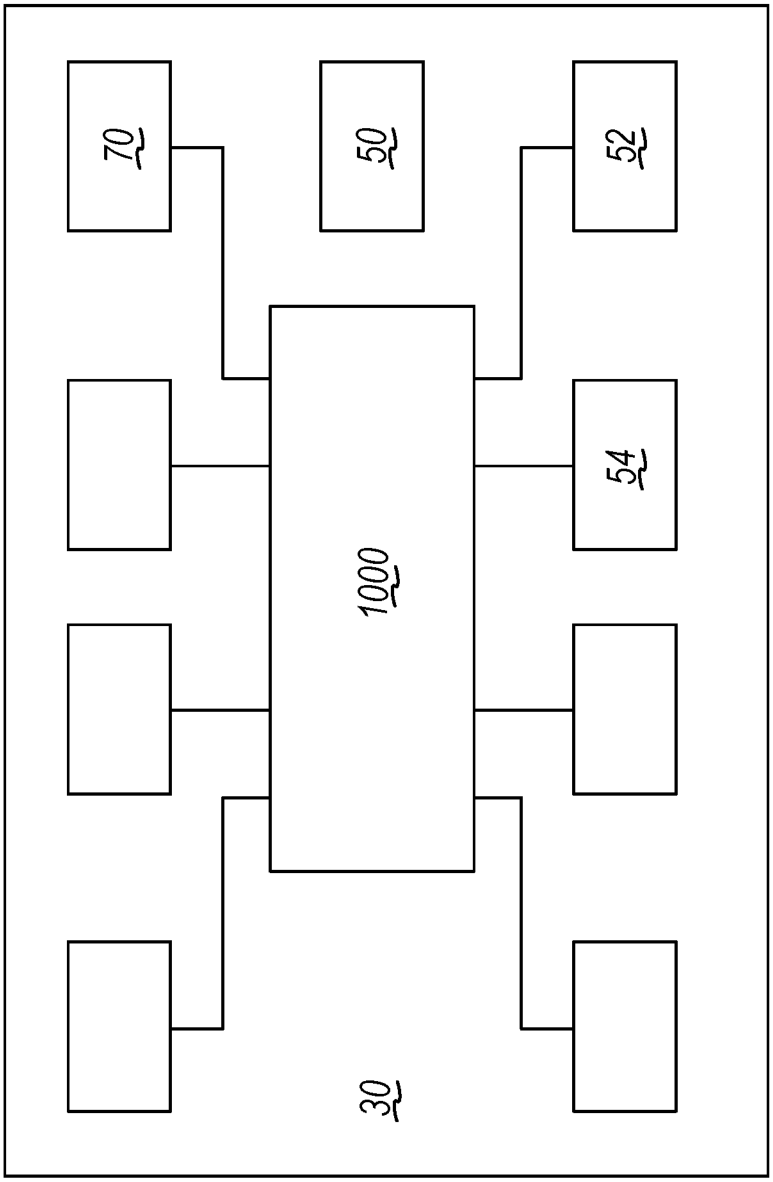
FIG. 3 depicts a schematic view of exemplary electrical and/or electromechanical components of the holster of FIG. 2.

Holster (30), shown schematically in FIG. 3, comprises vacuum pump (50), a motor (70), a control module (1000), a plurality of buttons (54), a vacuum sensor (52), and any other suitable electrical and/or electromechanical components. Vacuum pump (50) of the present example comprises a conventional diaphragm pump that is mechanically coupled to motor (70). Vacuum sensor (52) is coupled to vacuum pump (50) or along any vacuum path therefrom such that vacuum sensor (52) can determine the level of vacuum created by vacuum pump (50). Vacuum sensor (52) is electrically coupled to control module (1000) so that vacuum sensor (52) may output signals indicative of the vacuum level to control module (1000). In the configuration shown, motor (70) is operable to translate and/or rotate cutter (60) in response to actuation of one or more of buttons (54), as will be described below, and to activate vacuum pump (50), though this is merely optional and a second motor (not shown) may be provided to run vacuum pump (50). In particular, motor may be coupled to a cutter drive assembly (not shown) and may be activated by control module (1000) upon actuating one or more of buttons (54). Such a cutter drive assembly (not shown) may rotate gears (34, 36) simultaneously. As noted above, gears (34, 36) mesh with gears (310, 312) in probe (20) thus allowing motor (70) to translate and/or rotate cutter (60). Other various configurations for holster (30) may be provided as will be apparent to one of ordinary skill in the art in view of the teachings herein. By way of example only, the cutter drive assembly (not shown) and/or other features of holster (30) may be constructed in accordance with at least some of the teachings of U.S. Pat. No. 8,206,316 entitled "Tetherless Biopsy Device with Reusable Portion," issued Jun. 26, 2012; and/or U.S. Pat. No. 8,764,680, entitled "Handheld Biopsy Device with Needle Firing," issued Jul. 1, 2014, the disclosures of which are incorporated by reference herein.

III. Exemplary Probe

Figure 4:
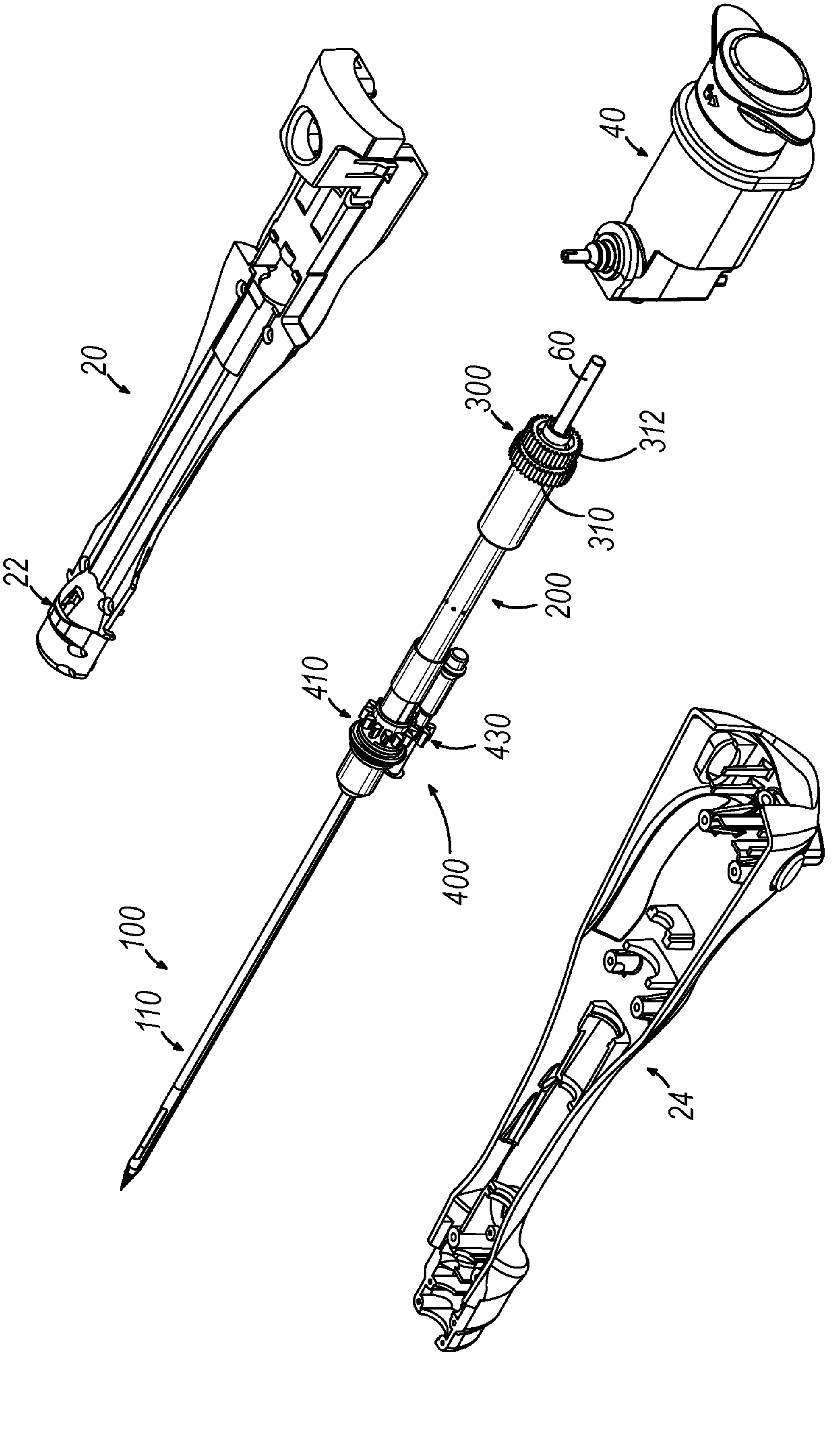
FIG. 4 depicts an exploded perspective view of the probe of FIG. 2.

FIG. 4 depicts a partially exploded view of probe (20) showing needle assembly (100), a cutter actuation assembly (300), a probe housing (22, 24) and tissue sample holder (40). Needle assembly (100) comprises a needle portion (110) and a valve assembly (200). As will be described in greater detail below, needle assembly (100) is generally operable to pierce tissue where cutter (60) can be positioned to sever a tissue sample from a patient and transport the tissue sample to tissue sample holder (40). More specifically, the needle portion (110) of needle assembly (100) is inserted into a patient's tissue. Cutter actuation assembly (300) is then operable to selectively actuate cutter (60) to an open position after pressing one or more of buttons (54). Once cutter (60) is actuated by cutter actuation assembly (300) into an open position, tissue may be prolapsed into needle portion (110) by means of a vacuum communicated through cutter (60). Cutter (60) may then be selectively actuated by means of cutter actuation assembly (300) into the closed position, severing the prolapsed tissue from the patient. Vent assembly (300) is then operable to selectively vent a portion of needle portion (110) to atmosphere thus creating a pressure differential between proximal and distal ends of the prolapsed tissue. The pressure differential then transports the prolapsed tissue through cutter (60) to tissue sample holder (40).

A. Exemplary Cutter Actuation Assembly

Cutter actuation assembly (300) comprises a series of gears (310, 312). Gears (310, 312) are configured to translate and/or rotate cutter (60). In the configuration shown, gears (310, 312) are coupled to motor (70) when probe (20) is attached to holster (30). In particular, two gears (310, 312) are controlled by motor (70) such that one gear (310) translates cutter (60) and another gear (312) rotates cutter (60) simultaneously. Other configurations may be provided utilizing different gear (310) arrangements. Moreover, configurations involving additional motors (70) may be used. Various suitable motor (70) and gear (310, 312) combinations will be apparent to one of ordinary skill in the art in view of the teachings herein. Indeed, cutter actuation assembly (300) may be constructed in accordance with at least some of the teachings of U.S. Pat. No. 8,206,316, entitled "Tetherless Biopsy Device with Reusable Portion," issued Jun. 26, 2012, the disclosure of which is incorporated by reference herein.

B. Exemplary Needle Portion

Figure 5:
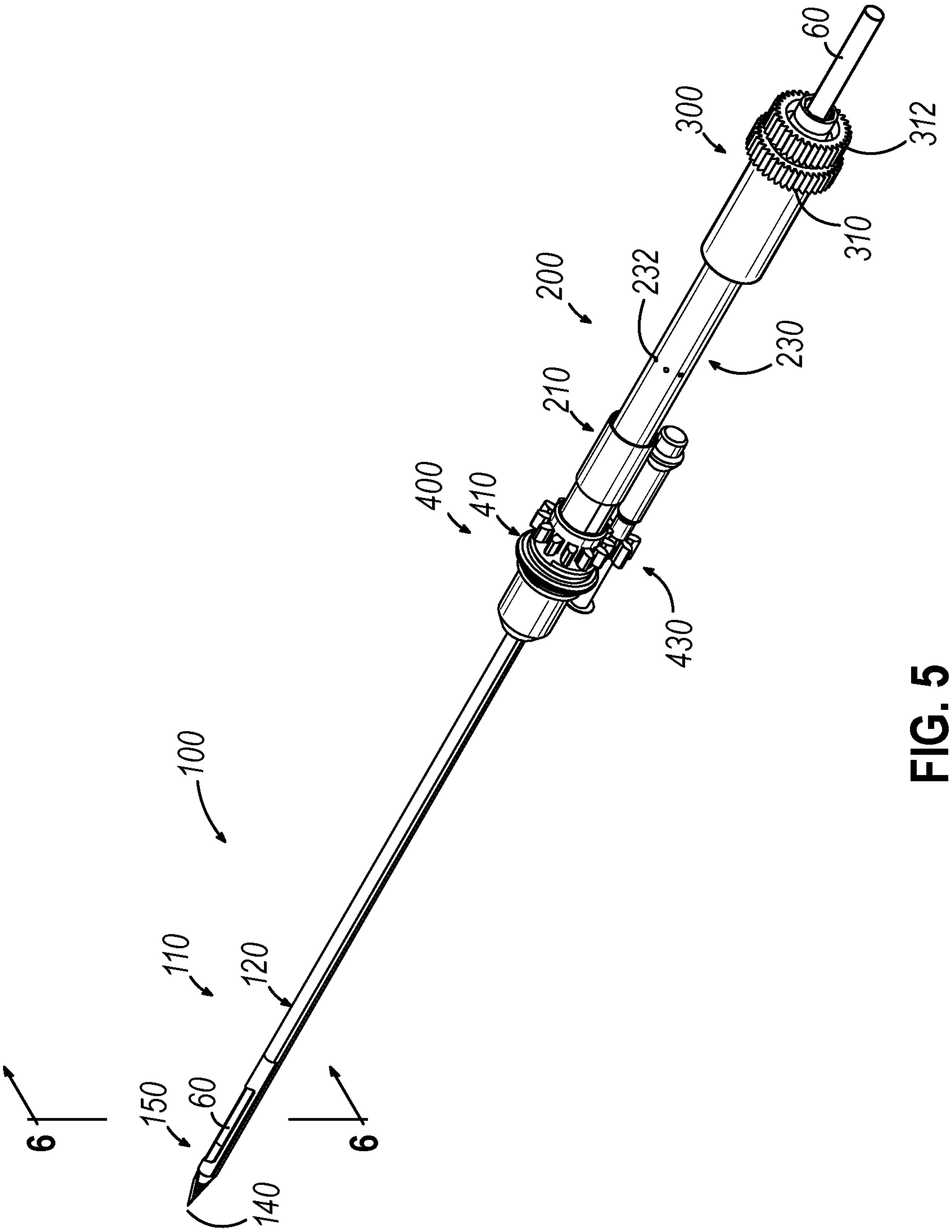
FIG. 5 depicts a perspective view of an exemplary needle assembly and associated components of the probe of FIG. 2.
Figure 6:
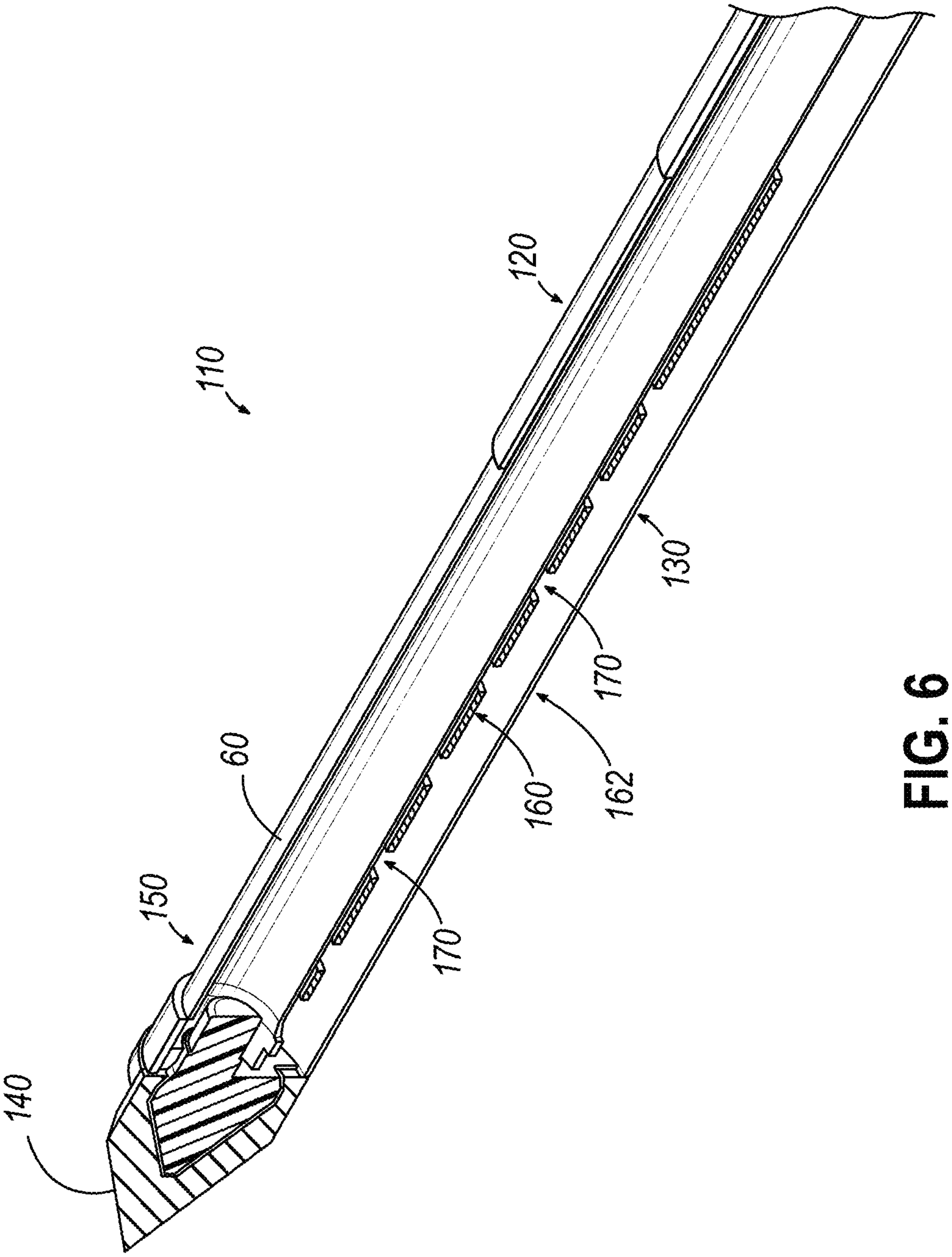
FIG. 6 depicts a cross-sectional perspective view of a distal end of the needle assembly of FIG. 5, taken along line 6-6 of FIG. 5.

FIGS. 5 and 6 show an exemplary needle portion (110). Needle portion (110) comprises a cannula (120), a partial cannula (130), a tissue piercing tip (140), and a lateral aperture (150). As is shown, cannula (120) is positioned on top of partial cannula (130). Cannula (120) and partial cannula (130) define a first lumen portion (160) and a second lumen portion (162). As is best seen in FIG. 6, cannula (120) is generally circular in shape while partial cannula (130) is semi-circular. Cannula (120) and partial cannula (130) may be coextensive with their proximal end terminating within the valve assembly (200) and their distal end supporting tissue piercing tip (140). Although needle portion (110) is shown as having a generally ovular cross-section, it should be understood that other cross-sectional shapes may be used. Indeed, needle portion (110) may be comprised of only circular tubes thus creating a generally figure eight cross-section. Alternatively, needle portion (110) may be comprised of two square tubes thus creating a generally square cross-section. Yet in other configurations, needle portion (110) may be comprised of two concentric tubes thus creating a generally circular cross-section. In still other configurations, any other suitable shape may be used.

FIG. 6 depicts needle portion (110) with cutter (60) disposed therein. In particular, cannula (120) is configured to receive cutter (60) and to permit cutter (60) to translate and rotate within second lumen portion (162). Cannula (120) further comprises lateral aperture (150). Lateral aperture (150) is sized to receive prolapsed tissue during operation of biopsy device (10). The sidewall of cannula (120) opposite lateral aperture (150) comprises a plurality of openings (170) that provide fluid communication between first lumen portion (160) and second lumen portion (162). In the present example, first lumen portion (160) may selectively provide atmospheric air to vent second lumen portion (162) through the plurality of openings (170). Such an atmospheric vent in second lumen portion (162) allows severed tissue to be drawn through cutter (60) and into tissue sample holder (40) under the influence of vacuum from vacuum pump (50).

In use, cutter (60) can be moved through a variety of positions such as a closed position, an open position and finally in an intermediate position. Each position may correspond to a particular stage in the tissue sample extraction process. For example, the cannula (120) may penetrate a patient's tissue when cutter (60) is in a closed position. In the closed position, cutter (60) is in its furthest distal position relative to lateral aperture (150). Thus, cannula (120) may penetrate through tissue smoothly without catching any surrounding tissue that might impede penetration. In the open position, cutter (60) is in its furthest proximal position relative to lateral aperture (150). This state may, for example, correspond to a position where cannula (120) is oriented inside a patient where a tissue sample may be taken. With cutter (60) in its furthest proximal position relative to lateral aperture (150) a vacuum may be applied to prolapse patient's tissue through lateral aperture (150). Finally, when cutter (60) is in the intermediate position, cutter (60) is in a position between its furthest distal and proximal positions relative to lateral aperture (150). In this position, cutter (60) may be in a motive state from either a closed position or an open position to a closed or open position, respectively. For example, cutter (60) can move from an open to closed position so that cutter (60) may sever a tissue sample. Alternatively, cutter can move from a closed to open position in order to allow the patient's tissue to prolapse through lateral aperture (150). As will be described in further detail below, these various positions correspond to various pneumatic states of valve assembly (200). It should be understood that the various positions of cutter (60) and the corresponding stages in the tissue extraction process are merely exemplary and other suitable combinations will be apparent to one of ordinary skill in the art from the teachings herein.

Tissue piercing tip (140) is shown as having a generally conical body with a flat blade protruding therefrom. The shape of tissue piercing tip (140) is merely exemplary and many other suitable shapes may be used. For example, tissue piercing tip (140) may be in the shape of a blade protruding from needle portion (110), disregarding the conical body. Still in further variations, the tissue piercing tip (140) may have a flat blade portion of varying shapes and configurations. Other various configurations for tissue piercing tip (140) and for needle portion (110) in general may be provided as will be apparent to one of ordinary skill in the art in view of the teachings herein. By way of example only, needle portion (110) may be constructed in accordance with at least some of the teachings of U.S. Pat. No. 8,801,742, entitled "Needle Assembly and Blade Assembly for Biopsy Device," issued Aug. 8, 2014, the disclosure of which is incorporated by reference herein.

C. Exemplary Valve Assembly

Figure 7:
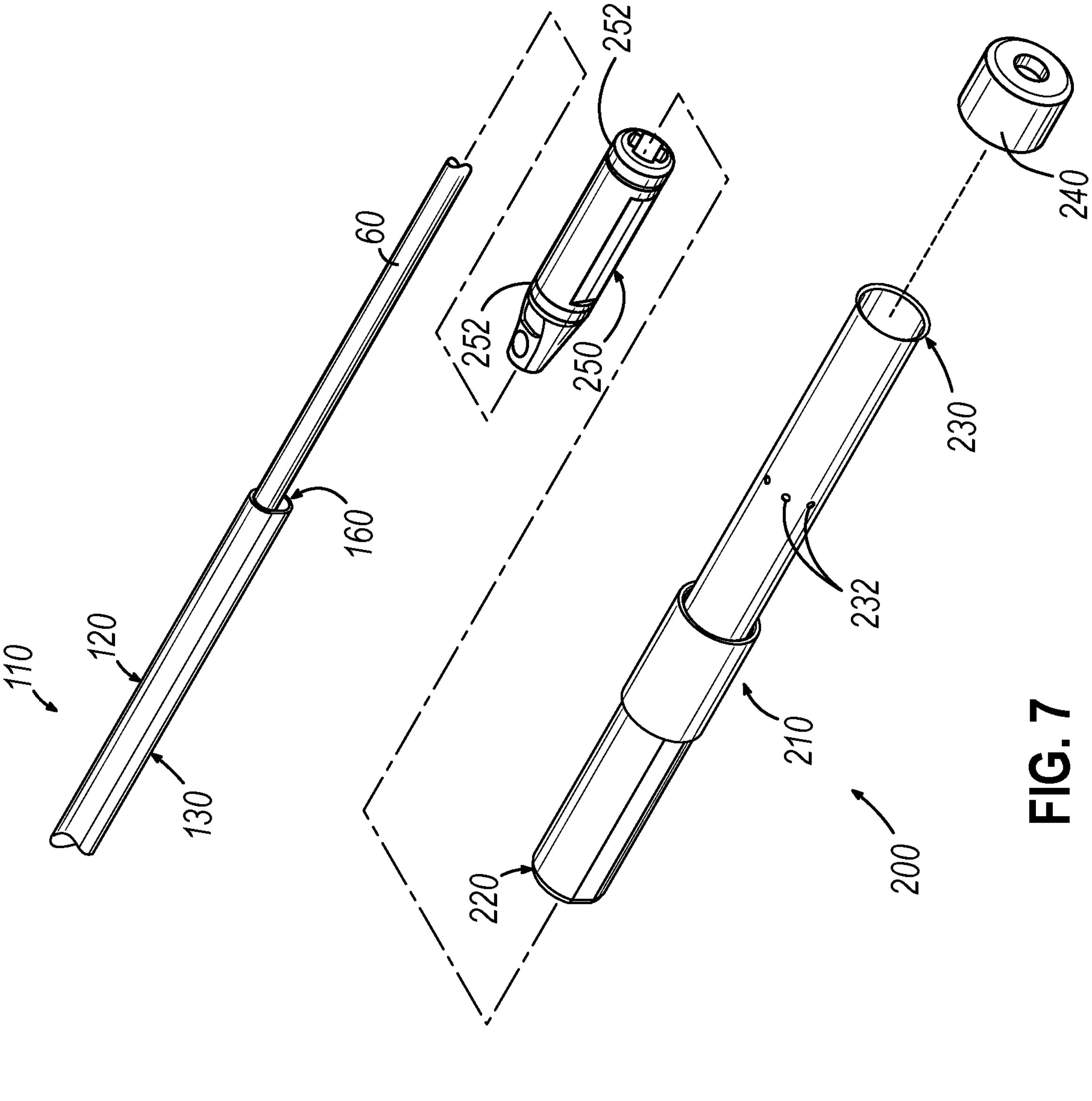
FIG. 7 depicts an exploded perspective view of the needle assembly of FIG. 5.

FIG. 7 depicts an exploded view of an exemplary valve assembly (200). Valve assembly (200) comprises a manifold (210), a static seal (240) and a spool body (250). Manifold (210) couples valve assembly (200) to the proximal end of needle portion (110) of needle assembly (100). In particular, manifold (210) comprises a needle coupling end (220) and a venting end (230). As is best seen in FIG. 7, needle coupling end (220) of manifold (210) is configured to receive the proximal end of needle portion (110) of needle assembly (100). In the present example, the coupling is made at the termination of cannula (120) and partial cannula (130). Cutter (60) then continues through valve assembly (200) to tissue sample holder (40). As will be described in more detail below, needle coupling end (220) creates an air tight seal around cannula (120) and partial cannula (130) to permit fluid flow from venting end (230) through first lumen portion (160). Coupling between needle portion (110) and needle coupling end (220) of manifold (210) may be facilitated by any suitable means such as adhesive bonding, a resilient sealing feature, an interference fitting, or a mechanical fastening means.

Venting end (230) extends proximally from needle coupling end (220). In the present example, needle coupling end (220) and venting end (230) are integrally formed as a single unit. In other examples, needle coupling end (220) and venting end (230) may be separate components joined together by any suitable fastening means. Venting end (230) terminates at the proximal end of manifold (210) where static seal (240) is affixed thereto. Venting end (230) defines a plurality of transverse openings (232) that are longitudinally co-located with each other. Transverse openings (232) are equidistantly spaced from each other about the outer perimeter of venting end (230) at their common longitudinal position. As will be described in greater detail below, transverse openings (232) provide communication of atmospheric air to the interior of venting end (230) such that atmospheric air can be fluidly communicated to first lumen portion (160).

Static seal (240) is affixed to the proximal end of manifold (210). Cutter (60) extends through static seal (240). Although cutter (60) is free to rotate and translate through static seal (240), static seal (240) prevents fluid communication at the interface between cutter (60) and static seal (240). Thus, with the seal created by static seal (240) and the seal created by needle coupling end (220), flow of atmospheric air can be limited to transverse openings (232) to first lumen portion (160).

Spool body (250) has o-rings (252) situated near the distal end and proximal end of spool body (250). As will be described in more detail below, o-rings (252) create a seal between spool body (250) and the inner diameter surface of venting end (230) of manifold (210). Although spool body (250) is shown with two o-rings (252), any suitable number of o-rings may be utilized. In some examples, spool body (250) can be connected directly to cutter (60) such that spool body (250) can more within manifold (210) as cutter (60) is moved. Additionally, in some examples spool body (250) can include one or more vent channels extending therethrough to promote fluid flow through spook body (250). By way of example only, spool body (250) may be constructed in accordance with at least some of the teachings of U.S. Pub. No. 2016/0287221, entitled "Biopsy Device with Translating Valve Assembly," published Oct. 6, 2016, the disclosure of which is incorporated by reference herein.

In use, spool body (250) is moved within manifold (210) relative to vent openings (232) to change the pneumatic state of valve assembly (200). In such uses, movement of spool body (250) can be at least partially controlled by movement of cutter (60). For instance, in some examples, valve assembly (200) can be configured to vent second lumen (162) when cutter (60) is disposed in a distal position. In such a position, spool body (250) is driven distally such that O-rings (252) are disposed distally of vent openings (232). Atmospheric air can then freely flow through vent openings (252) and spool body (250) into second lumen (162). Such a position can correspond to severing of a tissue sample using cutter (60). Thus, it should be understood that venting is provided to second lumen (162) after a tissue sample has been severed to promote tissue transport through cutter (60). In other examples, it may be desirable to substantially seal second lumen (162) relative to atmosphere. For instance, in the intermediate position described above, tissue may be prolapsed into lateral aperture (150). In this circumstance, it may be desirable to seal second lumen (162) to prevent escape of vacuum through vent openings (232). Accordingly, in this circumstance, spool body (250) can be positioned by cutter (60) such that O-rings (252) are positioned on distally and proximally relative to vent openings (232). O-rings (252) then seal second lumen (162) relative to atmosphere. Of course, various other additional or alternative pneumatic states can be used as will be apparent to those of ordinary skill in the art in view of the teachings herein. By way of example only, suitable pneumatic states can be in accordance with at least some of the teachings of U.S. Pub. No. 2016/0287221, entitled "Biopsy Device with Translating Valve Assembly," published Oct. 6, 2016, the disclosure of which is incorporated by reference herein.

D. Exemplary Needle Rotation Assembly

In some examples it may be desirable to rotate needle assembly (100) while collecting tissue samples. For instance, in some examples lateral aperture (150) is positioned within or adjacent to a suspect lesion. In such examples, it may be desirable to collect a tissue sample from each region 360° around needle portion (110) in order to collect the entire lesion as well as the margins between the lesion and healthy tissue.

In contexts where needle rotation is desired, it may also be desirable to rotate needle assembly (100) using a single hand. For instance, in some contexts one hand is used to hold biopsy device (10) while another hand is used to hold another instrument such as an ultrasound transducer. Thus, with both hands occupied, it may be desirable to rotate the needle with the hand holding the biopsy device to avoid having to release either the biopsy device itself or other instruments used in the biopsy procedure. Although various exemplary needle rotation assemblies are described below, it should be understood that various modifications can be made without departing from the spirit of the examples disclosed herein.

Figure 8:
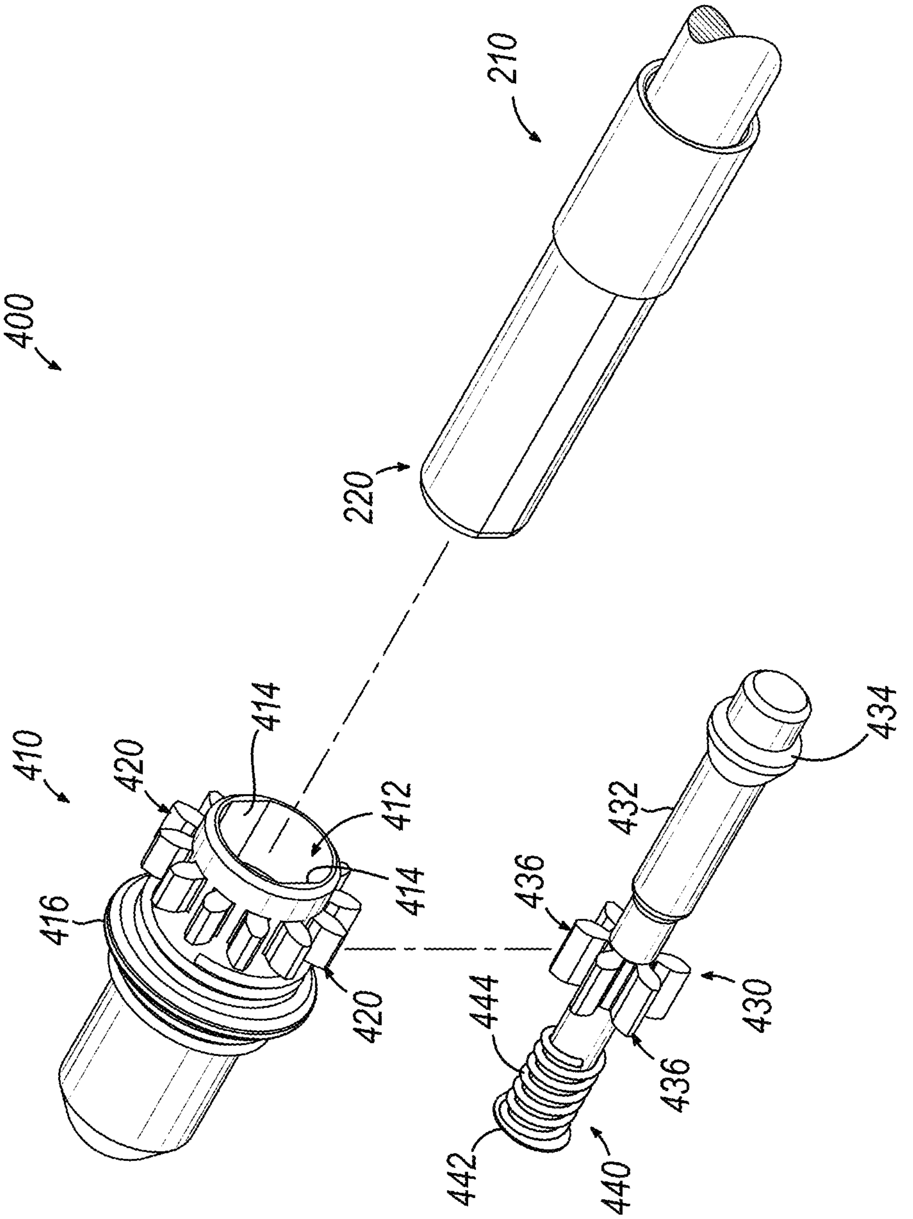
FIG. 8 depicts an exploded perspective view of an exemplary needle rotation assembly associated with the needle assembly of FIG. 5.

FIG. 8 shows an exemplary needle rotation assembly (400) that can be readily incorporated into biopsy device (10) described above. As can be seen, needle rotation assembly (400) includes a needle hub (410) and a pinion shaft (430). Needle hub (410) is configured to fit coaxially around cannula (120) of needle assembly (100) to thereby rotate needle assembly (100). As can be seen, needle hub (410) includes an open proximal end (412) sized to receive needle coupling end (220) of manifold (210). Open proximal end (412) includes two flat sides (414) that correspond to flat sides of manifold (210). Thus, it should be understood that rotation of needle hub (410) generally results in corresponding rotation of manifold (210). Since manifold (210) is fixedly secured to cannula (120), rotation of manifold (210) results in corresponding rotation of needle assembly (100).

Needle hub (410) further includes an alignment flange (416) extending outwardly from a cylindrical or oval-shaped body of needle hub (410). Alignment flange (416) is generally configured to interact with features of probe housing (22, 24) to hold needle hub (410) in a generally fixed position, while still permitting 360° rotation of needle hub (410). In the present example alignment flange (416) is generally integral with needle hub (410). However, it should be understood that in other examples alignment flange (416) can be configured as a separate part secured or fastened to the exterior of needle hub (410).

Needle hub (410) further includes a plurality of spur gear teeth (420) extending outwardly from the cylindrical or oval-shaped body of needle hub (410). As will be described in greater detail below, spur gear teeth (420) are generally configured to engage pinion shaft (430) to permit pinion shaft (430) to transfer rotation to needle hub (410). Spur gear teeth are oriented around the entire exterior of the body of needle hub (410) to permit 360 rotation of needle hub (410) by way of pinion shaft (430). Although the present example uses gear teeth to transfer rotational force, it should be understood that in other examples various alternative configurations can be used. For instance, in some examples rotation of needle hub (410) can be driven by a belt drive, a chain drive, or other means of transferring rotational force.

Pinion shaft (430) includes an elongate cylindrical shaft (432), a grip feature (434), a biasing mechanism (440), and a plurality of spur gear teeth (436) disposed between the grip feature and the biasing mechanism (440). Grip feature (434) is disposed near the proximal end of pinion shaft (430) and is generally configured for grasping by an operator for manipulation of pinion shaft (430) both rotationally and longitudinally. In the present example, grip feature (434) is generally conical in shape extending outwardly from shaft (432). Although grip feature (434) of the present example is shown as having a particular shape and configuration, it should be understood that in other examples grip feature (434) can take on a variety of shapes and/or configurations. For instance, in some examples, a plurality of protrusions can be added to grip feature (434) to further enhance the ability to achieve a grip of grip feature (434). In other examples, grip feature (434) can have a triangular shape, a square shape, a hexagonal shape, or various other shapes or combinations of shapes.

Spur gear teeth (464) are oriented around the exterior of cylindrical shaft (432) are generally configured to engage spur gear teeth (420) of needle hub (410) to transfer rotation of pinion shaft (430) to needle hub (410). Spur gear teeth (464) extend entirely around the exterior of shaft (432) to provide full 360° transfer of rotation. In the present example, the gear ratio between spur gear teeth (420) of needle hub (410) and spur gear teeth (436) of pinion shaft (430) is generally greater than 1. This configuration is such that multiple rotations of pinion shaft (430) are required for a single rotation of needle hub (410). In some examples, this is generally desirable to decrease the force input required to pinion shaft (430) for rotation of needle assembly (100). In the present example, the gear ratio is 2:1 such that needle hub (410) has 2 spur gear teeth (420) for every one spur gear tooth (436) of pinion shaft (430). However, it should be understood that in other examples various alternative gear ratios can be used such as 3:1, 4:1, 5:1, or etc.

Biasing mechanism (440) is disposed on the distal end of cylindrical shaft (432) and is generally configured to bias shaft (432) distally. As will be described in greater detail below, biasing of shaft (432) is generally configured to support a locking feature to prevent inadvertent rotation of needle assembly (100). Biasing mechanism (440) of the present example includes a biasing flange (442) and a coil spring (444). Biasing flange (442) is disposed on the distal end of shaft (432) and extends outwardly therefrom. Biasing flange (442) is generally configured to provide a backstop for coil spring (444) so that coil spring (444) can be loaded when shaft (432) is pulled proximally. Although not shown, it should be understood that coil spring (444) is generally disposed between biasing flange (442) and certain features of probe housing (22, 24). Thus, when shaft (432) is pulled proximally, coil spring is compressed between biasing flange (442) and probe housing (22, 24). Although coil spring (444) is shown and described herein as a coil spring, it should be understood that various alternative biasing mechanisms can be used such as a rubber band, an elastomeric cable, an elastomeric rod, and/or etc.

Figure 9:
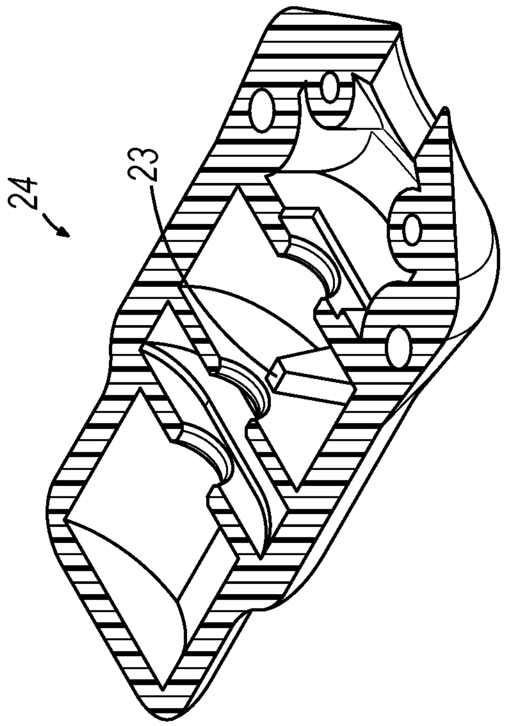
FIG. 9 depicts a detailed cross-sectional view of a probe housing of the biopsy device of FIG. 1.

FIG. 9 shows the interior of probe housing (24). As can be seen, in the present example the interior of probe housing (24) includes a lock protrusion (23). Lock protrusion (23) is generally configured to engage spur gear teeth (436) of pinion shaft (432). As will be described in greater detail below, engagement generally occurs when pinion shaft (432) is positioned in a distal position. When in this position, engagement between lock protrusion (23) and spur gear teeth (436) causes rotation of pinion shaft (430) to be locked, thereby locking rotation of needle assembly (100). Although lock protrusion (23) is shown as having a generally triangular shape in the present example, it should be understood that in other examples various alternative shapes can be used.

Figure 10A:
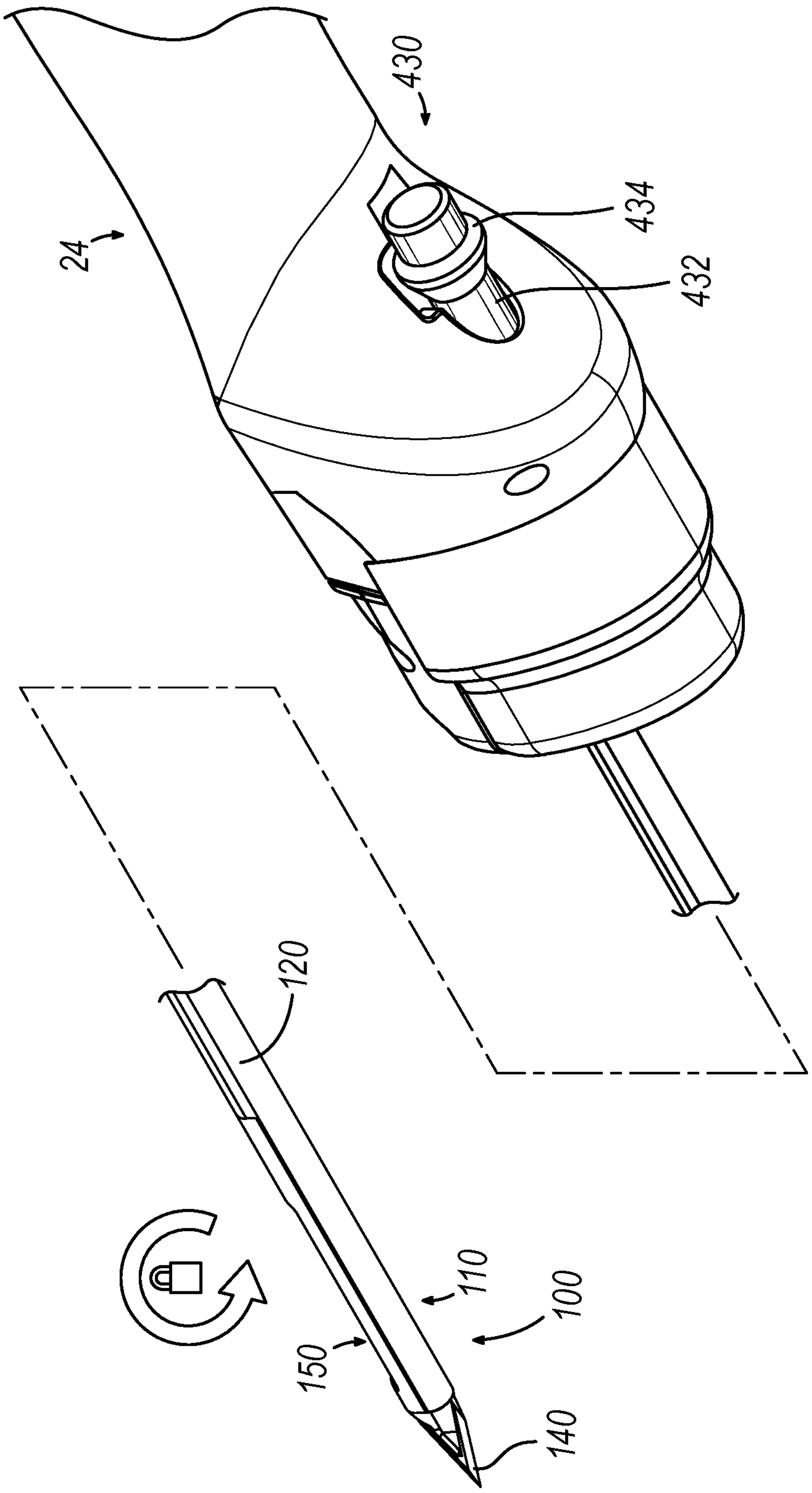
FIG. 10A depicts a perspective view of the biopsy device of FIG. 1, with the needle rotation assembly in a locked position.

FIGS. 10A through 11B show an exemplary use of needle rotation assembly (400) described above. As best seen in FIG. 10A, needle rotation assembly (400) is initially locked so that needle assembly (100) is in a fixed rotational position. In this position, pinion shaft (430) is in a distal position. As best seen in FIG. 11A, pinion shaft (430) is pushed distally by coil spring (444). This causes spur gear teeth (436) of pinion shaft (430) to engage lock protrusion (23) of probe housing (24). With spur gear teeth (436) of pinion shaft (430) engaged with lock protrusion (23), rotation of pinion shaft (430) is prevented.

When needle rotation assembly (400) is in the locked position, probe (20) can be used in a variety of ways. For instance, probe (20) can be initially attached to holster (30) and control module (1000) can initiate an initialization cycle including a sequence of retracting and advancing cutter (60). Once the initialization cycle is complete, an operator can insert needle portion (110) into a patient and orient needle portion (110) at or near a targeted lesion under a suitable form of imaging guidance such as ultrasound. Next at tissue sample can be collected by prolapsing tissue into lateral aperture (150) and advancing cutter (60) distally.

Figure 10B:
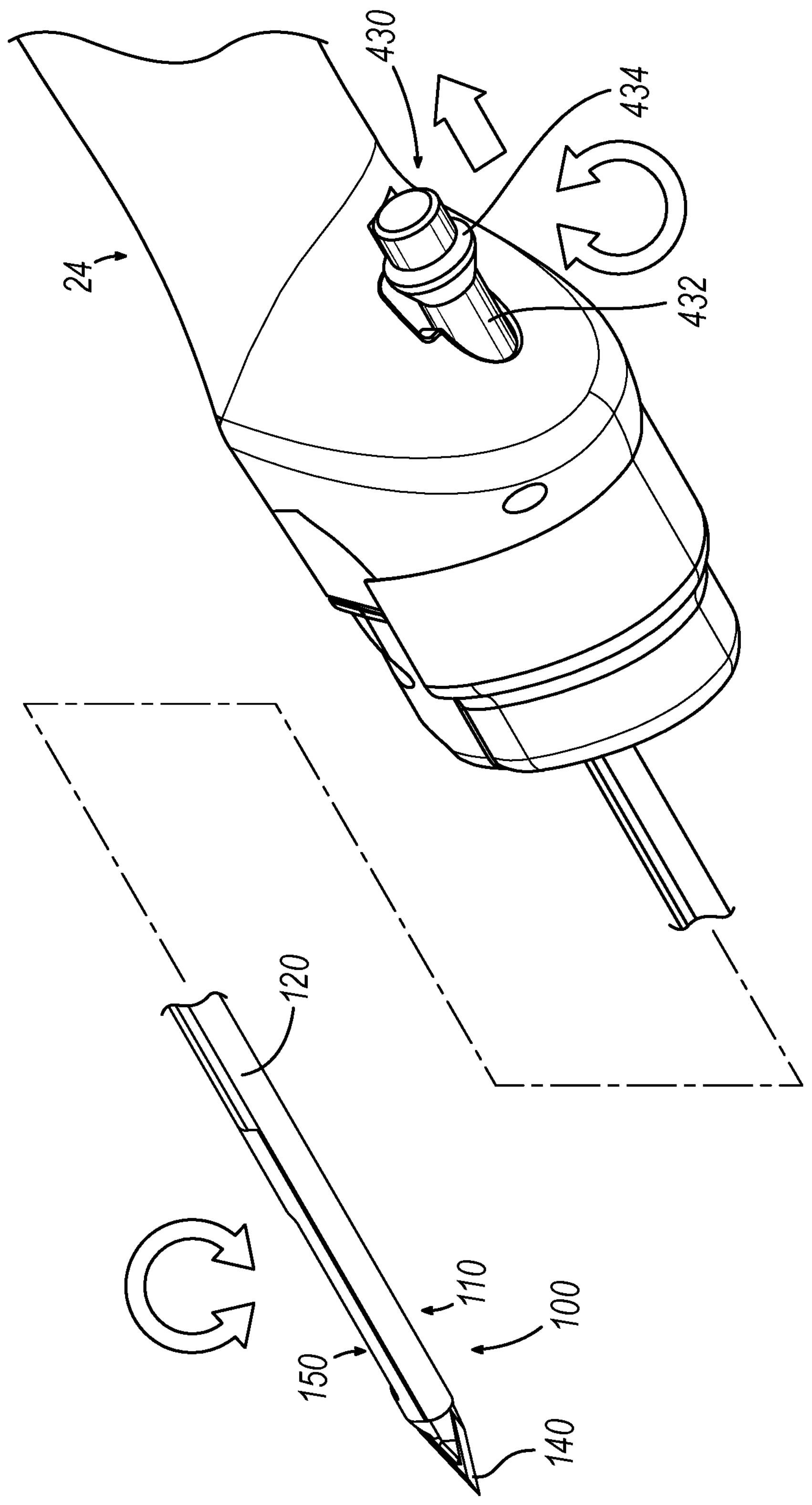
FIG. 10B depicts another perspective view of the biopsy device of FIG. 1, with the needle rotation assembly in an unlocked position.
Figure 11A:
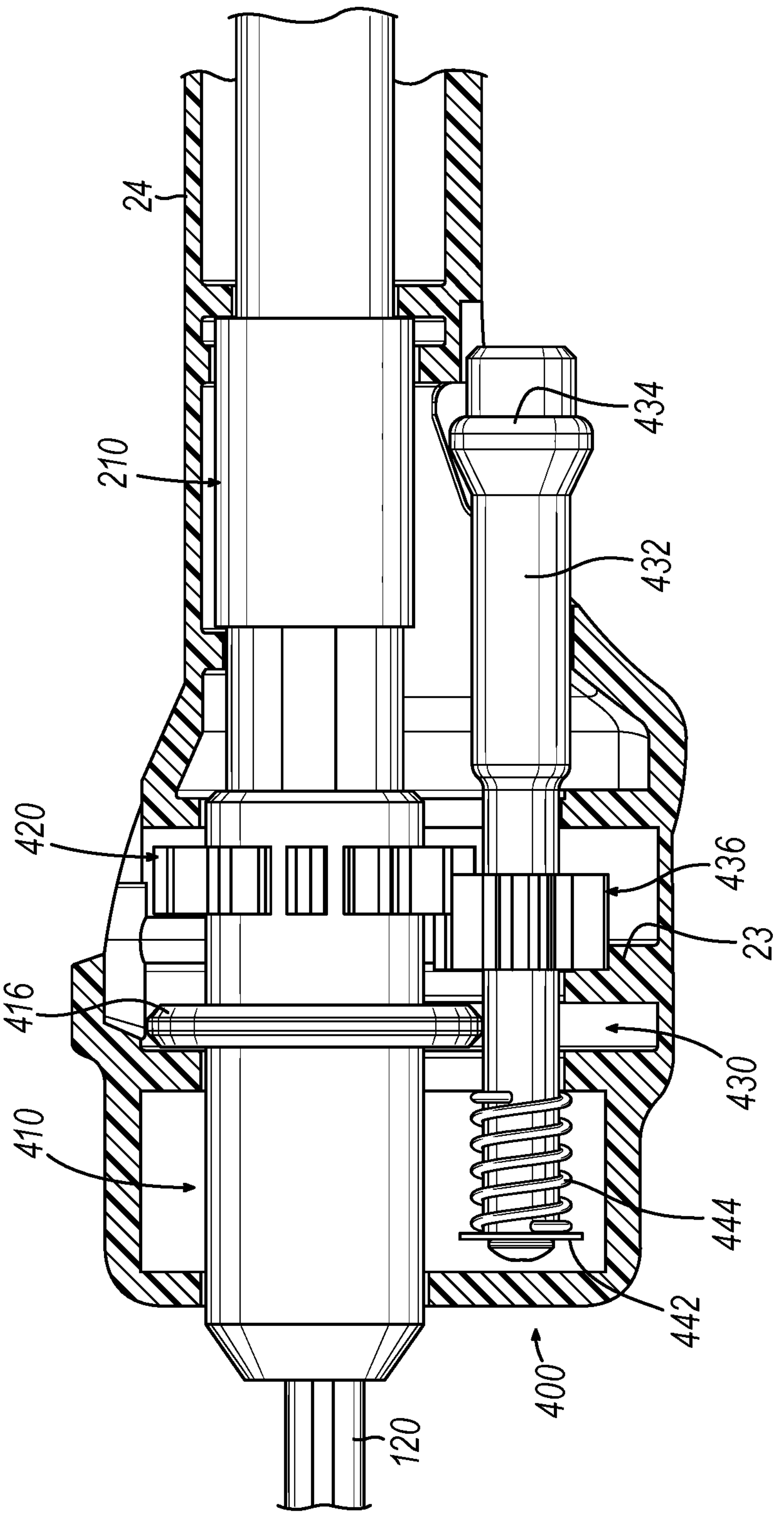
FIG. 11A depicts a side cut-away view of the biopsy device of FIG. 1, with the needle rotation assembly in the locked position.
Figure 11B:
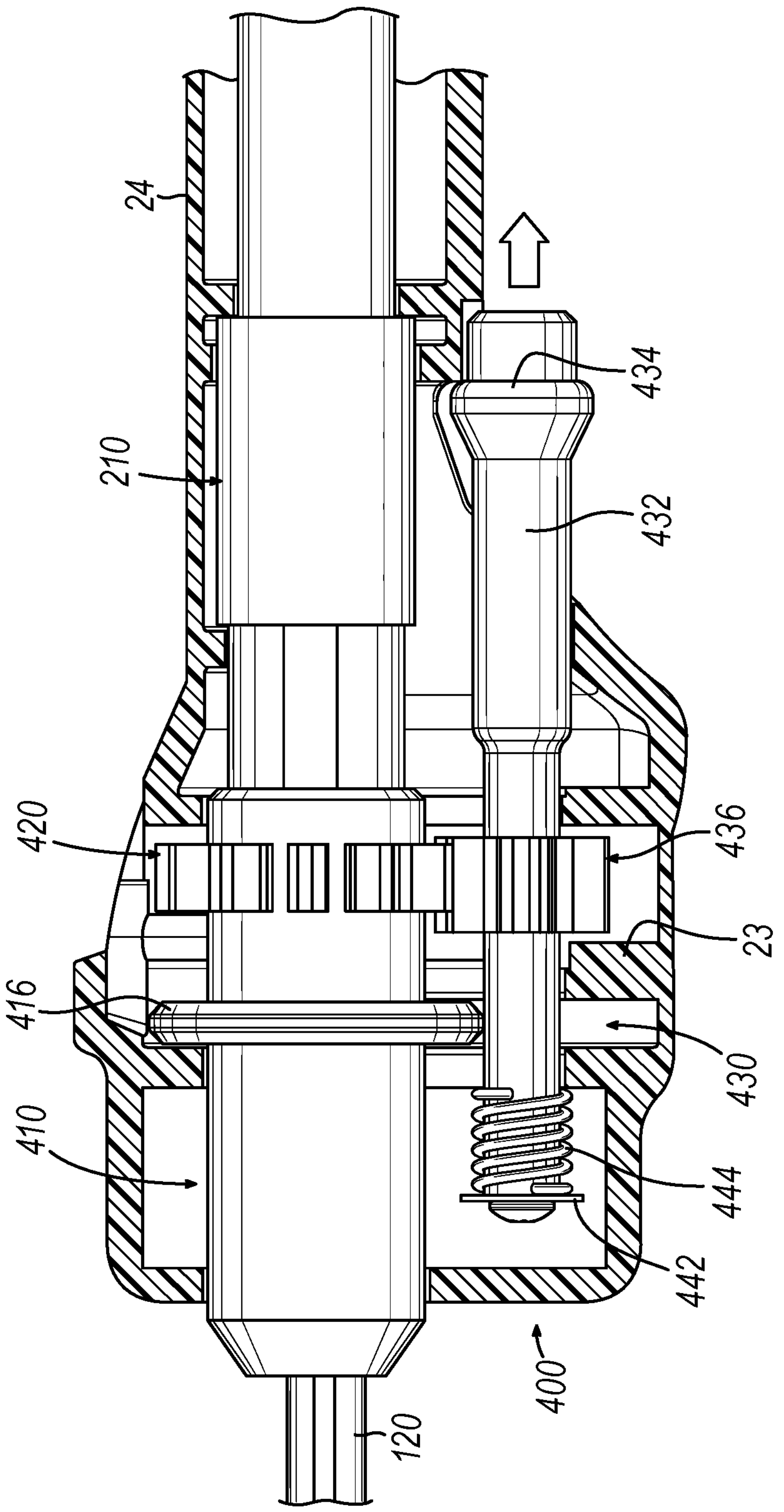
FIG. 11B depicts another side cut-away view of the biopsy device of FIG. 1, with the needle rotation assembly in the unlocked position.

Once an initial tissue sample has been collected, it may be desirable to rotate needle assembly (100) to reorient lateral aperture (150) and collect another tissue sample at a different location. To rotate needle assembly (100), an operator can pull pinion shaft (430) proximally to an unlocked position as shown in FIG. 10B. As seen in FIG. 11B, once pinion shaft (430) is pulled proximally, spur gear teeth (436) of pinion shaft (430) are released from lock protrusion (23) and pinion shaft (430) becomes fully rotatable in either a clockwise or counterclockwise direction to rotate needle assembly (100). In particular, pinion shaft (430) can be rotated to rotate spur gear teeth (436). Engagement between spur gear teeth (436) and spur gear teeth (420) the causes needle hub (410) to rotate. Rotation of needle hub (410) then results in rotation of manifold (210), which correspondingly rotates cannula (120) of needle assembly (100).

It should be understood that pinion shaft (430) is generally positioned relative to probe housing (24) in a position for single handed use of both needle rotation assembly (400) and the rest of biopsy device (10). For instance, in the position shown, grip feature (434) of pinion shaft (430) is positioned below buttons (54). This position can permit an operator to hold biopsy device (10) in a single hand and then use one or more fingers of the same hand to manipulate both buttons (54) and pinion shaft (430). By way of example only, in one use an operator can use an index finger of the hand gasping biopsy device (10) to both pull and rotate pinion shaft (430) in a single continuous motion. The same index finger can then be used to manipulate buttons (54).

Regardless of how an operator manipulates pinion shaft (430), once needle assembly (100) has been manipulated as desired, the operator can release pinion shaft (430) to return pinion shaft (430) to the locked position by way of the resilient bias provided by coil spring (444). Another subsequent tissue sample can be taken at the new needle position and the needle rotation process can then be repeated as many times as desired. Once all desired tissue samples have been taken, needle portion (110) can be removed from the patient and the biopsy procedure can be finalized.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device, the biopsy device comprising: a probe having a probe housing; a needle extending from the probe; a cutter disposed within the needle, wherein the cutter defines a cutter lumen and at least partially defines a vent lumen between an exterior of the cutter and an interior of the needle; and a manually actuated needle rotation assembly including a pinion shaft, wherein a portion of the pinion shaft is exposed relative to the probe housing such that the pinion shaft is configured for actuation using a single hand while grasping the biopsy device with the single hand.

Example 2

The biopsy device of Example 1, wherein the needle rotation assembly further includes a needle hub, wherein the needle hub is secured to the needle, wherein the needle hub is in mechanical communication with the pinion shaft to transfer rotary motion from the pinion shaft to the needle hub.

Example 3

The biopsy device of Example 2, wherein the pinion shaft includes a first gear, wherein the needle hub includes a second gear, wherein the first gear is configured to mesh with the second gear to transfer rotation of the pinion shaft to the needle hub.

Example 4

The biopsy device of Example 3, wherein the gear ratio between the second gear and the first gear is 2:1.

Example 5

The biopsy device of any one or more of Examples 1 through 4, wherein the needle rotation assembly further includes a biasing mechanism configured to bias the pinion shaft towards a locked position.

Example 6

The biopsy device of Example 5, wherein the pinion shaft is configured to engage a lock protrusion when in the locked position such that the protrusion prevents rotation of the pinion shaft.

Example 7

The biopsy device of Example 6, wherein the protrusion is a triangular portion extending from the probe housing towards the pinion shaft.

Example 8

The biopsy device of any one or more of Examples 1 through 4, wherein the needle rotation assembly further includes a biasing mechanism having a biasing flange and a coil spring, wherein the biasing flange is secured to the pinion shaft, wherein the coil spring is configured to drive the pinion shaft distally by the biasing flange.

Example 9

The biopsy device of Example 8, wherein the coil spring is coaxial with the pinion shaft.

Example 10

The biopsy device of any one or more of Examples 1 through 9, wherein the needle rotation assembly is configured to rotate the needle a full 360°.

Example 11

A method for using a biopsy device to rotate a needle associated with the biopsy device, the method comprising: grasping the biopsy device with a single hand; using one or more fingers of the single hand to pull a pinion shaft associated with the biopsy device proximally to an unlocked position; rotating the needle by rotating the pinion shaft while holding the pinion shaft in the unlocked position.

Example 12

The method of Example 11, further comprising inserting the needle into tissue of a patient while grasping the biopsy device with the single hand.

Example 13

The method of Example 12, further comprising collecting a tissue sample after inserting the needle into the tissue.

Example 14

The method of Example 13, wherein the step of rotating the needle is performed after collecting the tissue sample.

Example 15

A biopsy device, the biopsy device comprising: a probe having a probe housing; a needle extending from the probe; a cutter disposed within the needle, wherein the cutter defines a cutter lumen and at least partially defines a vent lumen between an exterior of the cutter and an interior of the needle; and a manually actuated needle rotation assembly including a shaft and a needle actuator, wherein the shaft includes an actuation portion configured to engage the needle actuator, wherein the shaft is resiliently biased toward a distal position, wherein the shaft is configured such that the actuation portion is positioned distally of the needle actuator when the shaft is in the distal position.

Example 16

The biopsy device of Example 15, wherein the needle actuator is coaxial with the needle.

Example 17

The biopsy device of Examples 15 or 16, wherein the shaft is configured for manual movement from the distal position to a proximal position.

Example 18

The biopsy device of Example 17, wherein the shaft is configured such that the actuation portion engages the needle actuator when the shaft is moved to the proximal position from the distal position.

Example 19

The biopsy device of any one or more of Examples 15 through 18, wherein the needle rotation assembly further includes a coil spring, wherein the shaft further includes a biasing flange, wherein the coil spring is positioned between the biasing flange and a portion of the probe housing.

Example 20

The biopsy device of Example 19, wherein the coil spring is coaxial with the shaft.

Example 21

The biopsy device of any one or more of Examples 15 through 20, wherein the needle actuator comprises a first gear, wherein the actuation portion comprises a second gear.

Example 22

The biopsy device of Example 21, wherein the gear ratio between the first gear and the second gear is 2:1.

Example 23

The biopsy device of any one or more of Examples 15 through 22, wherein the needle rotation assembly is configured to rotate the needle a full 360°.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, the biopsy device comprising:

(a) a probe having a probe housing;

(b) a needle extending from the probe;

(c) a cutter disposed within the needle, wherein the cutter defines a cutter lumen and at least partially defines a vent lumen between an exterior of the cutter and an interior of the needle; and (d) a manually actuated needle rotation assembly including a pinion shaft, wherein a portion of the pinion shaft is exposed relative to the probe housing such that the pinion shaft is configured for actuation using a single hand while grasping the biopsy device with the single hand, the needle rotation assembly including a locking protrusion configured to selectively lock rotation of the pinion shaft, the pinion shaft being configured to move proximally relative to the locking protrusion to disengage the locking protrusion and thereby rotate relative to the locking protrusion.

2. The biopsy device of claim 1, wherein the needle rotation assembly further includes a needle hub, wherein the needle hub is secured to the needle, wherein the needle hub is in mechanical communication with the pinion shaft to transfer rotary motion from the pinion shaft to the needle hub.

3. The biopsy device of claim 2, wherein the pinion shaft includes a first gear, wherein the needle hub includes a second gear, wherein the first gear is configured to mesh with the second gear to transfer rotation of the pinion shaft to the needle hub.

4. The biopsy device of claim 3, wherein the gear ratio between the second gear and the first gear is 2:1.

5. The biopsy device of claim 1, wherein the needle rotation assembly further includes a biasing spring configured to bias the pinion shaft towards a locked position.

6. The biopsy device of claim 5, wherein the pinion shaft is configured to engage the locking protrusion when in the locked position such that the locking protrusion prevents rotation of the pinion shaft.

7. The biopsy device of claim 6, wherein the locking protrusion is a triangular portion extending from the probe housing towards the pinion shaft.

8. The biopsy device of claim 1, wherein the needle rotation assembly further includes a biasing mechanism having a biasing flange and a coil spring, wherein the biasing flange is secured to the pinion shaft, wherein the coil spring is configured to drive the pinion shaft distally by the biasing flange.

9. The biopsy device of claim 8, wherein the coil spring is coaxial with the pinion shaft.

10. The biopsy device of claim 1, wherein the needle rotation assembly is configured to rotate the needle a full 360°.

11. A biopsy device, the biopsy device comprising:

(a) a probe having a probe housing;

(b) a needle extending from the probe;

(c) a cutter disposed within the needle, wherein the cutter defines a cutter lumen and at least partially defines a vent lumen between an exterior of the cutter and an interior of the needle; and (d) a manually actuated needle rotation assembly including a shaft and a needle actuator, wherein the shaft includes an actuation portion comprising gear teeth configured to engage the needle actuator, wherein the shaft is resiliently biased toward a distal position, wherein the shaft is configured such that the actuation portion is positioned distally of the needle actuator when the shaft is in the distal position, wherein the needle rotation assembly includes a locking protrusion configured to selectively lock rotation of the shaft when the shaft is in the distal position.

12. The biopsy device of claim 11, wherein the needle actuator is coaxial with the needle.

13. The biopsy device of claim 11, wherein the shaft is configured for manual movement from the distal position to a proximal position.

14. The biopsy device of claim 13, wherein the shaft is configured such that the actuation portion engages the needle actuator when the shaft is moved to the proximal position from the distal position.

15. The biopsy device of claim 11, wherein the needle rotation assembly further includes a coil spring, wherein the shaft further includes a biasing flange, wherein the coil spring is positioned between the biasing flange and a portion of the probe housing.

16. The biopsy device of claim 11, wherein the needle actuator comprises a first gear, wherein the actuation portion comprises a second gear.

* * * * *